US006242571B1

(12) United States Patent
Knowles et al.

(10) Patent No.: US 6,242,571 B1
(45) Date of Patent: Jun. 5, 2001

(54) SEROLOGICAL IDENTIFICATION OF CATTLE, SHEEP OR GOATS INFECTED WITH ANAPLASMA SPECIES

(76) Inventors: Donald P. Knowles, SE. 1020 Kamiaken; Travis C. McGuire, SW. 920 Crestview; Guy H. Palmer, 615 SE. High St.; William C. Davis, NW. 300 Yates; Terry F. McElwain, SE. 925 Glen Echo, all of Pullman, WA (US) 99163

( * ) Notice: Subject to any disclaimer, the term of this patent is extended or adjusted under 35 U.S.C. 154(b) by 0 days.

(21) Appl. No.: 09/099,613

(22) Filed: Jun. 18, 1998

Related U.S. Application Data

(62) Division of application No. 08/730,995, filed on Oct. 16, 1996, now Pat. No. 5,798,219, which is a continuation of application No. 08/156,426, filed on Nov. 23, 1993, now abandoned.

(51) Int. Cl.[7] .............................. C07K 1/00; C07H 21/04

(52) U.S. Cl. .......................... 530/350; 530/822; 536/23.7

(58) Field of Search ................................ 536/23.1, 23.7; 530/350, 822

(56) References Cited

U.S. PATENT DOCUMENTS 4,134,792 1/1979 Boguslaski et al. .

OTHER PUBLICATIONS

N. Tebele, T. McGuire and G. Palmer, "Induction of Protective Immunity by Using *Anaplasma marginale* Initial Body Membranes," *Infection and Immunity* 59:3199–3204 (1991).

E. Visser, T. McGuire, G. Palmer, W.C. Davis, V. Shkap, E. Pipano and D.P. Knowles Jr., "The *Anaplasma marginale msp5* Gene Encodes a 19–Kilodalton Protein Conserved in all Recognized Anaplasma Species," *Infection and Immunity* 60:5139–5144 (Dec. 1992).

J. Anderson, "Use of Monoclonal Antibody in a Blocking ELISA to Detect Group Specific Antibodies to Bluetongue Virus," *Journal of Immunological Methods* 74:139–149 (1984).

E. Harlow and D. Lane, "Antibodies: A Laboratory Manual," *Cold Spring Harbor Laboratory* (N.Y.) pp. 342 and pp. 511–552 (1988).

G.H. Palmer, A.F. Barbet, A.J. Musoke, J.M. Katende, F. Rurangirwa, V. Shkap, E. Pipano, W.C. Davis and T. McGuire, "Recognition of Conserved Surface Protein Epitopes on *Anaplasma Centrale* and *Anaplasma Marginale* Isolates from Israel, Kenya and the United States," *Int. Journal for Parasitology* 18(1):33–38 (1988).

*Primary Examiner*—Patricia A. Duffy
(74) *Attorney, Agent, or Firm*—Margaret A. Connor; M. Howard Silverstein; John D. Fado

(57) ABSTRACT

The subject invention concerns the use of the conserved *Anaplasma marginale* major surface protein 5 gene and gene product and monoclonal antibody ANAF16C1 for the identification of animals persistently infected with Anaplasma species.

3 Claims, 2 Drawing Sheets

1 2 3 4 5 6 7 8 9 10 11
200 ▸

97.4 ▸
68 ▸

43 ▸

29 ▸

14.3 ▸

US 6,242,571 B1

SEROLOGICAL IDENTIFICATION OF CATTLE, SHEEP OR GOATS INFECTED WITH ANAPLASMA SPECIES

This application is a division of pending application Ser. No. 08/730,995, field Oct. 16, 1996 U.S. Pat. No. 5,998,219, which is a continuation of Ser. No. 08/156,426, filed Nov. 23, 1993, abandoned. The prior applications are hereby incorporated here in by reference.

FUNDING

U.S. Department of Agriculture Cooperative Agreement-58-5348-1-178 & U.S. Department of Agriculture Cris Work Unit 5348-32000-009-00D

BACKGROUND OF INVENTION

Anaplasmosis, a vector-borne rickettsial disease of cattle, sheep and goats is caused by three species; *Anaplasma marginale, Anaplasma centrale* and *Anaplasma ovis*. Clinical disease is characterized by anemia, weight loss, abortion and death. Survivors are lifelong carriers of the rickettsia. Eventual control of Anaplasma species infection will require both an effective vaccine and identification of carrier cattle, sheep or goats. Two possible methods for routine carrier identification are a nucleic acid probe for hybridization of infected blood or the detection of Anaplasma species-specific antibody is serum. Hybridization of DNA extracted from blood with an *Anaplasma marginale*-specific nucleic acid probe does not always detect known carriers, because of cyclic changes in rickettsemia levels. Carrier identification by antibody requires that infected animals never clear the rickettsia. Indefinite persistence of *Anaplasma marginale* in infected cattle has been documented. Current serological tests for anaplasmosis are not widely used, primarily because the error rate is high. One problem with current tests is false positive results caused by erythrocyte contamination of the *Anaplasma marginale* antigen used in the tests, and the presence of anti-erythrocyte antibody in the sera of some cattle.

Recently, progress has been made toward the characterization of a surface membrane protein of *Anaplasma marginale* for use in diagnosis (N. Tebele, T. C. McGuire, and G. H. Palmer, Infect. Immun. 59:3199–3204, 1991 and E. S. Visser, T. C. McGuire, G. H. Palmer, W. C. Davis, V. Shkap, E. Pipano, and D. P. Knowles, Jr., Infect. Immun. 60:5139–5144, 1992.). This protein, designated major surface protein 5 (MSP-5) and monoclonal antibody ANAF16C1 were shown to have utility when used together in the competitive inhibition enzyme-linked immunosorbent assay (CI-ELISA) format (Anderson, J. Immunol. Meth., 74:139–149, 1984) for the diagnosis of cattle, sheep and goats infected with *Anaplasma marginale, Anaplasma centrale* and *Anaplasma ovis* (E. S. Visser, T. C. McGuire, G. H. Palmer, W. C. Davis, V. Shkap, E. Pipano, and D. P. Knowles, Jr., Infect. Immun. 60:5139–5144, 1992.).

BRIEF SUMMARY OF THE INVENTION

Disclosed and claimed here is a CI-ELISA using monoclonal antibody ANAF16C1 and the corresponding protein, *Anaplasma marginale* major surface protein-5, bound by monoclonal antibody ANAF16C1 for the identification of cattle, sheep or goats persistently infected with *Anaplasma marginale, Anaplasma centrale* or *Anaplasma ovis*. This invention provides a means of identifying cattle, sheep, or goats that are persistently infected with *Anaplasma marginale, Anaplasma centrale* or *Anaplasma ovis*. This test is specific for Anaplasma species detection since the specificity of this CI-ELISA resides solely in monoclonal antibody ANAF16C1 and monoclonal antibody ANAF16C1 as been shown to specifically bind to only Anaplasma species MSP-5. Since MSP-5 is conserved in all known Anaplasma species, it is logical to assert that MSP-5 is conserved in all isolates of Anaplasma species.

BRIEF DESCRIPTION OF THE SEQUENCES

SEQ ID NO:1 is the DNA sequence of *Anaplasma marginale* major surface protein 5.

SEQ ID NO:2 is the amino acid sequence of *Anaplasma marginale* major surface protein 5.

DETAILED DESCRIPTION OF THE INVENTION

Figure 2:
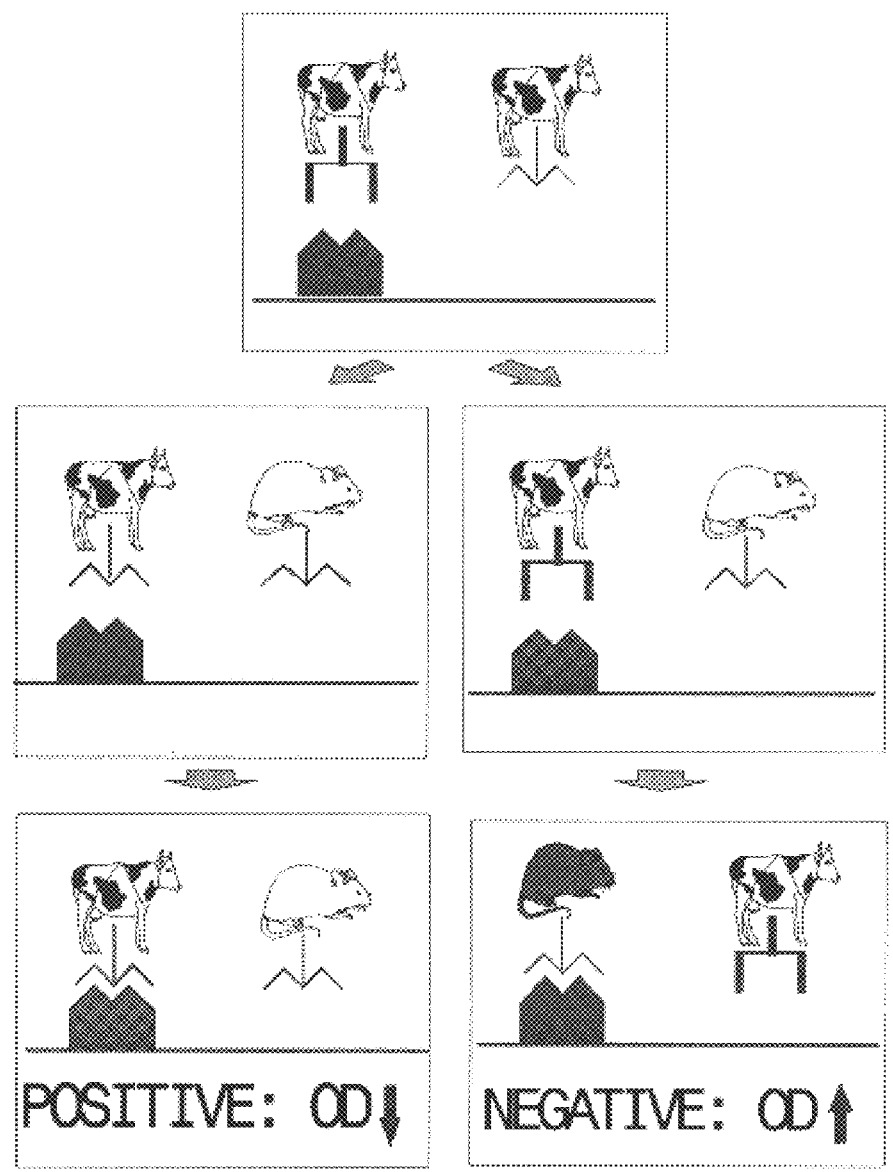
FIG. 2 is a diagram of the CI-ELISA using monoclonal antibody ANAF16C1 (mouse), Anaplasma marginale major surface protein 5 (▲▲), and test serum (cow).

The subject invention pertains to the use of monoclonal antibody ANAF16C1 and Anaplasma major surface protein 5 in a CI-ELISA format (FIG. 2) for the serological detection of cattle, sheep or goats infected with *Anaplasma marginale, Anaplasma centrale*, or *Anaplasma ovis*. Hybridoma ANAF16C1 which produces and secretes monoclonal antibody ANAF16C1 was deposited on Dec. 2, 1997, with the American Type Culture Collection (ATCC), 12301 Parklawn Drive, Rockville, Md. 20852 USA, under terms of the Budapest Treaty, and has been assigned the accession number ATCC HB-12440.

Figure 1:
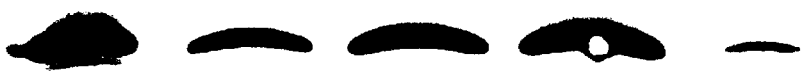
FIG. 1 is an immunoblot demonstrating the binding of monoclonal antibody ANAF16C1 to major surface protein 5 of: Florida strain of *Anaplasma marginale* (lane 2); Israeli strain *Anaplasma centrale* (lane 4); Israeli non-tailed strain of *Anaplasma marginale* (lane 6); Israeli trailed strain of *Anaplasma marginale* (lane 8), Idaho strain of Anaplasma ovis (lane 10).

The evidence that MSP-5 is effective in the CI-ELISA format for the diagnosis of animals infected with Anaplasma species are: (i) MSP-5 is conserved in all known Anaplasma species (FIG. 1); (ii) all immune sera tested from animals infected with Anaplasma species bind to MSP-5, and (iii) all immune sera tested from animals infected with Anaplasma species compete with monoclonal antibody ANAF16C1 for binding to MSP-5.

The evidence that monoclonal antibody ANAF16C1 is effective in the CI-ELISA format for the diagnosis of animals infected with Anaplasma species are: (i) monoclonal antibody ANAF16C1 binds to MSP-5 in all known Anaplasma species; (ii) monoclonal antibody ANAF16C1 binds to both native and recombinant MSP-5, and (iii) all immune sera tested from animals infected with Anaplasma species compete with monoclonal antibody ANAF16C1 for binding to MSP-5.

MATERIALS AND METHODS

The Florida strain of *Anaplasma marginale* from which native and recombinant MSP-5 were derived originated from a pooled blood sample collected from naturally infected cattle in various sections of Florida in 1955 (M. Ristic and C. A. Carson, In L. H. Miller, J. A. Pino, and J. J. McKelvey (ed.), Immunity to blood parasites of animals and man. Plenum Publishing Corp., New York, 1997).

Native MSP-5 was obtained from blood stabilates by differential centrifugation as described (G. H. Palmer and T. C. McGuire, J. Immun. 133:1010–1015, 1984). Briefly, 20 milliliters of stabilate was thawed at 37° C. for 10 min and then washed 3 times by suspension in 40 ml of RPMI 1640 media (Flow Laboratories, McLean, Va.) containing 2 mM 1-Glutamine and 25 mM HEPES, with centrifugation at 27,000×G. The sediment was resuspended in 35 ml of media, disrupted by 2 min of sonication at 50 W (127×4 mm titanium probe, Braun-Sonic 1510; Braun Instruments, San Francisco, Calif.), and was washed two times at 1650×G for 15 min.

Recombinant MSP-5 (SEQ ID NO:2) was prepared from a 50-ml overnight culture of *E. coli* XL1-Blue containing pAM104 in LB broth with 50 μg of ampicillin per ml. Molecular clone pAM104 contains the msp5 gene with the nucleotide sequence of MSP-5 presented in SEQ ID NO:1. A bacterial lysate prepared with PI buffer (50 mM Tris [pH 8.0], 5 mM EDTA, 5 mM iodoacetamide, 0.1 mM N-a-p-tosyl-L-lysine chloromethyl ketone 1 mM phenylmethylsulfonyl fluoride, 1 mg of lysozyme per ml, 1% Nonidet P-40).

Monoclonal antibody ANAF16C1 was made by fusing X63-Ag8.653 murine myeloma cells (J. F. Kearney, A. Radbruch, B. Liesegang, and K. Rajewsky, J. Immunol. 123:1548–1550, 1979) with spleen cells from BALB/c mice immunized with purified initial bodies of the Florida strain of *Anaplasma marginale*. An immunoglobulin G2a monoclonal antibody that immunoprecipitated a 19 kDa protein from 125I-surface-radiolabeled solubilized initial bodies was designated ANAF16C1. Monoclonal antibody ANAF16C1 was conjugated with horseradish peroxidase as described (A. G. Farr and P. K. Nakane, J. Immun. Meth. 47:129–144, 1981).

The CI-ELISA format was first described in 1984 (J. Anderson, J. Immunol. Meth., 74:139–149, 1984). An overview of the use of the CI-ELISA format for the detection of animals infected with Anaplasma species is as follows: (i) Immulon 2 plates are coated with native or recombinant MSP-5; (ii) plate is incubated overnight at RT; (iii) the plate is rinsed and blocker is added (1 hour); (iv) test sera are incubated with antigen (15 min); (v) monoclonal antibody ANAF16C1 conjugated to horseradish peroxidase is added and incubated for 15 min; (vi) wells are rinsed and substrate (p-nitrophenyl phosphate) is added (10 min), and (vii) the reaction is stopped and the optical density is read at 490.

The specifics of the CI-ELISA using monoclonal antibody ANAF16C1 and MSP-5 for serological detection of animals infected with Anaplasma species are as follows. Preparation of all buffers and reagents are provided below. Wells of Immulon 2 plate (Dynatech Laboratories, Chantilly, Va.) are coated with sufficient native or recombinant MSP-5 to provide and $OD_{490}$ reading of between 1.0 and 1.5. The appropriate dilution of initial body lysate (native msp-5) or bacterial lysate applied to an Immulon 2 plate (recombinant MSP-5) is determined by titration with monoclonal antibody ANAF16C1. After plates are coated with the appropriate amount of MSP-5 lysate, the Immulon 2 plates are sealed with acetate and incubated overnight at room temperature. The well contents are removed and the wells rinsed once with 200 ul of PBS/Tween. Coated plates are blocked by adding 200 μl blocking buffer, and incubating for 1 hr at room temperature. Blocker is removed from the plates and 40 μl of undiluted test serum is added to each well and incubated for 15 min at room temperature. Conjugated monoclonal antibody ANAF16C1 is then added at the appropriate concentration determined previously by titration. Conjugated monoclonal antibody ANAF16C1 is diluted such that the appropriate quantity of conjugates monoclonal antibody ANAF16C1 is added in 10 μl. The mixture is incubated for 15 min at room temperature. Contents are removed from the wells and the wells are rinsed twice with 200 μl of PBS/Tween and once with substrate buffer. Fifty μl of OPD substrate is added per well and incubated for 10 min at room temperature. The reaction is stopped by adding 25 μl of 3 N HCl per well. The $OD_{490}$ is read.

What are claimed are:

1. An isolated acid sequence which encodes a polypeptide having an amino acid sequence shown in SEQ ID NO:2.

2. An isolated acid sequence encoding a polypeptide, said nucleic acid having a nucleotide sequence shown in SEQ ID NO:1.

3. Isolated *Anaplasma marginale* major surface protein 5 having an amino acid sequence shown in SEQ ID NO:2, said protein free of other Anaplasma protein.

* * * * *

UNITED STATES PATENT AND TRADEMARK OFFICE
CERTIFICATE OF CORRECTION

PATENT NO.     : 6,242,571 B1
DATED          : June 5, 2001
INVENTOR(S)    : Donald P. Knowles et al.

It is certified that error appears in the above-identified patent and that said Letters Patent is hereby corrected as shown below:

<u>Title page,</u>
Insert: -- [73] Assignees: The United States of America as represented by the Secretary of Agriculture, Washington, D.C.
Washington State University Research Foundation, Pullman, WA --

Signed and Sealed this

Sixth Day of May, 2003

JAMES E. ROGAN
*Director of the United States Patent and Trademark Office*

```
                       SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
         (A) LENGTH: 1146 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Anaplasma marginale
         (C) INDIVIDUAL ISOLATE: Florida (ix) FEATURE:
         (A) NAME/KEY: CDS
         (B) LOCATION: 118..750
         (D) OTHER INFORMATION: /product= "major surface protein 5"
```

-continued (xi) SEQUENCE DESCRIPTION: SEQ ID NO:1:

```
GTATACTCAG TTGCGCCTGG CGCTTGACCA ACCTGGGCAT AGGTGCTACG ATCGCGCCTG      60

CTCGTTTTGC CGTCCGGCAA TGTGGCGCAT TTTTGAGTGT TCGTTGGGGT GTGATAG       117
```

| ATG | AGA | ATT | TTC | AAG | ATT | GTG | TCT | AAC | CTT | CTG | CTG | TTC | GTT | GCT | GCC | 165 |
|---|---|---|---|---|---|---|---|---|---|---|---|---|---|---|---|---|
| Met | Arg | Ile | Phe | Lys | Ile | Val | Ser | Asn | Leu | Leu | Leu | Phe | Val | Ala | Ala | |
| 1 | | | | 5 | | | | | 10 | | | | | 15 | | |

| GTG | TTC | CTG | GGG | TAC | TCC | TAT | GTG | AAC | AAG | AAA | GGC | ATT | TTC | AGC | AAA | 213 |
|---|---|---|---|---|---|---|---|---|---|---|---|---|---|---|---|---|
| Val | Phe | Leu | Gly | Tyr | Ser | Tyr | Val | Asn | Lys | Lys | Gly | Ile | Phe | Ser | Lys | |
| | | | 20 | | | | | 25 | | | | | 30 | | | |

| ATC | GGC | GAG | AGG | TTT | ACC | ACT | TCC | GAA | GTT | GTA | AGT | GAG | GGC | ATA | GCC | 261 |
|---|---|---|---|---|---|---|---|---|---|---|---|---|---|---|---|---|
| Ile | Gly | Glu | Arg | Phe | Thr | Thr | Ser | Glu | Val | Val | Ser | Glu | Gly | Ile | Ala | |
| | | 35 | | | | | 40 | | | | | 45 | | | | |

| TCC | GCG | TCT | TTC | AAC | AAT | TTG | GTT | AAT | CAC | GAG | GGG | GTC | ACC | GTC | AGT | 309 |
|---|---|---|---|---|---|---|---|---|---|---|---|---|---|---|---|---|
| Ser | Ala | Ser | Phe | Asn | Asn | Leu | Val | Asn | His | Glu | Gly | Val | Thr | Val | Ser | |
| 50 | | | | | 55 | | | | | 60 | | | | | | |

| AGC | GGC | GAT | TTT | GGC | GGC | AAG | CAC | ATG | TTG | GTA | ATA | TTC | GGC | TTC | TCA | 357 |
|---|---|---|---|---|---|---|---|---|---|---|---|---|---|---|---|---|
| Ser | Gly | Asp | Phe | Gly | Gly | Lys | His | Met | Leu | Val | Ile | Phe | Gly | Phe | Ser | |
| 65 | | | | 70 | | | | | 75 | | | | | 80 | | |

| GCC | TGT | AAG | TAC | ACG | TGC | CCT | ACC | GAG | TTA | GGC | ATG | GCT | TCT | CAG | CTC | 405 |
|---|---|---|---|---|---|---|---|---|---|---|---|---|---|---|---|---|
| Ala | Cys | Lys | Tyr | Thr | Cys | Pro | Thr | Glu | Leu | Gly | Met | Ala | Ser | Gln | Leu | |
| | | | 85 | | | | | 90 | | | | | 95 | | | |

| CTA | AGT | AAA | CTA | GGC | GAC | CAT | GCC | GAT | AAG | TTG | CAA | GTT | GTG | TTC | ATA | 453 |
|---|---|---|---|---|---|---|---|---|---|---|---|---|---|---|---|---|
| Leu | Ser | Lys | Leu | Gly | Asp | His | Ala | Asp | Lys | Leu | Gln | Val | Val | Phe | Ile | |
| | | | 100 | | | | | 105 | | | | | 110 | | | |

| ACT | GTT | GAT | CCG | AAA | AAT | GAC | ACC | GTA | GCC | AAG | CTT | AAA | GAG | TAC | CAC | 501 |
|---|---|---|---|---|---|---|---|---|---|---|---|---|---|---|---|---|
| Thr | Val | Asp | Pro | Lys | Asn | Asp | Thr | Val | Ala | Lys | Leu | Lys | Glu | Tyr | His | |
| | | | 115 | | | | | 120 | | | | | 125 | | | |

| AAG | TCT | TTT | GAT | GCG | AGA | ATT | CAG | ATG | CTC | ACA | GGC | GAA | GAA | GCA | GAC | 549 |
|---|---|---|---|---|---|---|---|---|---|---|---|---|---|---|---|---|
| Lys | Ser | Phe | Asp | Ala | Arg | Ile | Gln | Met | Leu | Thr | Gly | Glu | Glu | Ala | Asp | |
| | | 130 | | | | | 135 | | | | | 140 | | | | |

| ATA | AAG | AGC | GTG | GTT | GAA | AAC | TAC | AAG | GTG | TAT | GTG | GGC | GAC | AAG | AAG | 597 |
|---|---|---|---|---|---|---|---|---|---|---|---|---|---|---|---|---|
| Ile | Lys | Ser | Val | Val | Glu | Asn | Tyr | Lys | Val | Tyr | Val | Gly | Asp | Lys | Lys | |
| 145 | | | | | 150 | | | | | 155 | | | | | 160 | |

| CCA | AGT | GAT | GGT | GAT | ATC | GAC | CAC | TCA | ACG | TTC | ATG | TAC | CTC | ATC | AAT | 645 |
|---|---|---|---|---|---|---|---|---|---|---|---|---|---|---|---|---|
| Pro | Ser | Asp | Gly | Asp | Ile | Asp | His | Ser | Thr | Phe | Met | Tyr | Leu | Ile | Asn | |
| | | | 165 | | | | | 170 | | | | | 175 | | | |

| GGG | AAA | GGC | AGG | TAT | GTC | GGG | CAT | TTT | GCG | CCA | GAT | TTT | AAC | GCG | TCT | 693 |
|---|---|---|---|---|---|---|---|---|---|---|---|---|---|---|---|---|
| Gly | Lys | Gly | Arg | Tyr | Val | Gly | His | Phe | Ala | Pro | Asp | Phe | Asn | Ala | Ser | |
| | | | 180 | | | | | 185 | | | | | 190 | | | |

| GAG | GGC | CAA | GGC | GAG | GAG | CTG | TTT | AAG | TTT | GTC | AGC | GGT | CAC | ATG | CTT | 741 |
|---|---|---|---|---|---|---|---|---|---|---|---|---|---|---|---|---|
| Glu | Gly | Gln | Gly | Glu | Glu | Leu | Phe | Lys | Phe | Val | Ser | Gly | His | Met | Leu | |
| | | | 195 | | | | | 200 | | | | | 205 | | | |

| AAT | TCT | TAG | TTAAGCATGG | CAGTGGTACA | GTTTCGTGTG | TCGGTCGTCC | 790 |
|---|---|---|---|---|---|---|---|
| Asn | Ser | * | | | | | |
| | 210 | | | | | | |

```
TTGTGAGGCA GTAGAAAGTA TGGGGCTTTG GGGGCTTTCC TTTGTGGCGT TGTCGCGCT     850

TGCGTTAGGA GCTGGGGCTG ACCAGATCAG GGTGGTTGGC TCTTCCACCG TGTTCCATT     910

TATCTCTTCT GTTGCCGAAG AGTTTGGTAG ATTCTCCGCC TATAGAACCC CGTCATAGA     970

GTCCGTGGGA AGTGGCATGG GCTTTAACAT GTTTTGCGCT GGCAGCAGCA GTGATACACC   1030

AGACATAGCC ATGTCCTCTA GGCGCATCAA GGATGCAGAA GTCGAACTTT GCGGCATGAA   1090

TGGCGTGAAG GACATGATCG AGATAGGTCT GGGCTACGAC GGCATAGCCC GAATTC       1146
```

(2) INFORMATION FOR SEQ ID NO:2:

(i) SEQUENCE CHARACTERISTICS:
  (A) LENGTH: 210 amino acids (B) TYPE: amino acid
        (D) TOPOLOGY: linear (ii) MOLECULE TYPE: protein (xi) SEQUENCE DESCRIPTION: SEQ ID NO:2:

```
Met Arg Ile Phe Lys Ile Val Ser Asn Leu Leu Phe Val Ala Ala
 1               5                  10                  15

Val Phe Leu Gly Tyr Ser Tyr Val Asn Lys Lys Gly Ile Phe Ser Lys
                20                  25                  30

Ile Gly Glu Arg Phe Thr Thr Ser Glu Val Val Ser Glu Gly Ile Ala
             35                  40                  45

Ser Ala Ser Phe Asn Asn Leu Val Asn His Glu Gly Val Thr Val Ser
         50                  55                  60

Ser Gly Asp Phe Gly Gly Lys His Met Leu Val Ile Phe Gly Phe Ser
 65                  70                  75                  80

Ala Cys Lys Tyr Thr Cys Pro Thr Glu Leu Gly Met Ala Ser Gln Leu
                 85                  90                  95

Leu Ser Lys Leu Gly Asp His Ala Asp Lys Leu Gln Val Val Phe Ile
                100                 105                 110

Thr Val Asp Pro Lys Asn Asp Thr Val Ala Lys Leu Lys Glu Tyr His
                115                 120                 125

Lys Ser Phe Asp Ala Arg Ile Gln Met Leu Thr Gly Glu Glu Ala Asp
                130                 135                 140

Ile Lys Ser Val Val Glu Asn Tyr Lys Val Tyr Val Gly Asp Lys Lys
145                 150                 155                 160

Pro Ser Asp Gly Asp Ile Asp His Ser Thr Phe Met Tyr Leu Ile Asn
                165                 170                 175

Gly Lys Gly Arg Tyr Val Gly His Phe Ala Pro Asp Phe Asn Ala Ser
                180                 185                 190

Glu Gly Gln Gly Glu Glu Leu Phe Lys Phe Val Ser Gly His Met Leu
                195                 200                 205

Asn Ser
    210
```